United States Patent [19] [11] 4,398,045
Sebag [45] Aug. 9, 1983

[54] POLYETHYLENE GLYCOL DERIVATIVES, THEIR USE AND COSMETIC AND PHARMACEUTICAL COMPOSITIONS CONTAINING THEM

[75] Inventor: Henri Sebag, Paris, France
[73] Assignee: L'Oreal, Paris, France
[21] Appl. No.: 309,811
[22] Filed: Oct. 8, 1981

[30] Foreign Application Priority Data
Oct. 10, 1980 [FR] France ................. 80 21776

[51] Int. Cl.³ .................. C07C 43/11; C07C 43/10
[52] U.S. Cl. .................. 568/624; 252/170; 252/174.21; 252/351; 252/307; 252/DIG. 1; 252/DIG. 13; 424/365; 424/63; 424/70; 424/73; 424/71; 8/405; 568/616; 568/620
[58] Field of Search ................. 568/624, 620, 616

[56] References Cited
U.S. PATENT DOCUMENTS 3,036,118   5/1902   Jackson et al. ............... 568/624
3,057,890  10/1962   DeGroote ..................... 568/620
3,802,905   4/1974   Beyer et al. ................. 568/624
4,061,869  12/1977   Schwarze et al. ............. 568/620

Primary Examiner—Howard T. Mars
Attorney, Agent, or Firm—Cushman, Darby & Cushman

[57] ABSTRACT

The invention relates to new polyethylene glycol derivatives.

These compounds correspond to the general formula:

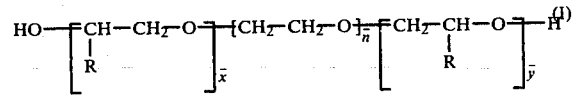

in which R denotes an alkyl and/or alkoxymethyl and/or alkenyloxymethyl radical or a mixture of these radicals, $\bar{n}$ denotes an average number of units from 20 to 500 and preferably from 30 to 200, and $\bar{x}$ and $\bar{y}$ denote average numbers of units from 0 to 8, it being possible for ($\bar{x}+\bar{y}$) to vary from 1 to 8.

They can be used in cosmetic or pharmaceutical compositions, in particular as thickeners.

7 Claims, No Drawings

POLYETHYLENE GLYCOL DERIVATIVES, THEIR USE AND COSMETIC AND PHARMACEUTICAL COMPOSITIONS CONTAINING THEM

The present invention relates to products derived from polyethylene glycols and from alkylene oxides and/or from alkyl glycidyl ethers or alkenyl glycidyl ethers, their use and cosmetic and/or pharmaceutical compositions in which they are used.

Pharmaceutical and cosmetic compositions intended for use by topical application generally have a high viscosity, being presented in the form of oils, gels, creams or pastes.

This type of presentation is highly valued by the consumer; for the formulator, it most frequently satisfies a practical requirement, namely that of limiting the diffusion of the product, for locally applied compositions, to the treatment zone.

This requirement is particularly important for medicinal compositions, especially if it is desired to carry out local treatments, and it is equally real for the formulation of cosmetic compositions such as compositions intended for hair dyeing, which must not trickle onto the forehead or the neck, and of shampoos in concentrated form, which must not run into the user's eyes, and also for all the other topical applications for which it is desirable to limit the application of the composition to well-defined areas.

A certain number of thickening products have been used in the past for obtaining this result, in particular natural gums and synthetic anionic or cationic polymers.

The use of inorganic salts for increasing the viscosity of solutions of anionic surface-active agents has also been described.

However, it has been found that certain of these products are ineffective for thickening solutions based on surface-active agents, or compositions already containing polymers which flocculate on the addition of ionic thickeners.

Mixtures of polyethylene glycol monoesters and diesters have also been proposed as non-ionic thickeners for cosmetic compositions. However, the proportions of monoesters and diesters are difficult to control; in particular, these products are unstable, which results in a drop in the viscosity of the solutions as a function of time.

A new class of non-ionic compounds which can be used for increasing the viscosity of solutions of ionic or non-ionic surface-active agents has now been discovered, according to the present invention. By virtue of their non-ionic nature, they are more readily compatible with other ionic constituents. Furthermore, they have the great advantage of being chemically stable and of making it possible to obtain viscosities which are substantially constant as a function of time, at ambient temperature or at elevated temperatures.

The products of the invention are solubilised or dispersed in water at concentrations from about 20 to 60%, to give transparent or opaque gels. At lower concentrations, a separation into two phases is generally observed, one phase being gelled and the other completely fluid. However, the introduction of, say, 0.2 to 10% of products of this invention into solutions of surface-active agents makes it possible to obtain limpid or opalescent, homogeneous compositions of substantially increased viscosity.

In certain cases, the products of the invention can be used as foam synergistic agents.

The products can, in certain cases, reduce the aggressiveness of surface-active agents which can be present in certain cosmetic compositions such as soaps, shampoos, eye make-up removal lotions, and foam baths, for example.

The invention thus provides new derivatives of polyethylene glycols and of alkylene oxides and/or of alkyl glycidyl ethers or alkenyl glycidyl ethers, these products essentially being characterised in that they correspond to the general formula (I):

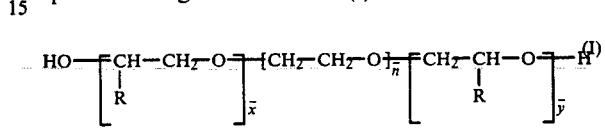

in which R denotes an alkyl and/or alkoxymethyl and/or alkenyloxymethyl radical or a mixture of these radicals, $\bar{n}$ denotes an average number of units from 20 to 500 and preferably from 30 to 200, and $\bar{x}$ and $\bar{y}$ denote average numbers of units from 0 to 8 and preferably from 1 to 8, it being possible for the sum $(\bar{x}+\bar{y})$ to vary from 1 to 8, preferably from 2 to 8 and in particular from 2 to 6.

The alkyl radicals are preferably linear radicals having 8 to 18 carbon atoms; the alkoxymethyl or alkenyloxymethyl radicals preferably contain from 8 to 20 carbon atoms in the alkyl or alkenyl part.

The products according to the invention thus essentially consist of a polyoxyethyleneated sequence which is joined, at least at one end and preferably at both ends, to a very limited number of lipophilic units, the proportion by weight of the oxyethyleneated part desirably representing 70 to 95% of the product.

These products can be obtained, in particular, by adding one or more compounds of the general formula:

in which R has the same meaning as given above, to mixtures of polyethylene glycols, in the presence of a basic catalyst.

Specific epoxides of the formula (II) which can be used include:

1,2-alkylene oxides such as 1,2-decene oxide, 1,2-dodecene oxide, 1,2-tetradecene oxide, 1,2-hexadecene oxide or 1,2-octadecene oxide; alkyl glycidyl ethers such as decyl glycidyl ether, dodecyl glycidyl ether, tetradecyl glycidyl ether, hexadecyl glycidyl ether, octadecyl glycidyl ether, eicosyl glycidyl ether, 2-methyldodecyl glycidyl ether, 2-methyltetradecyl glycidyl ether, 2-methylpentadecyl glycidyl ether, 2-hexyldecyl glycidyl ether or 2-octyldodecyl glycidyl ether, 2-ethylhexylglycidyl ether; oleyl glycidyl ether, undecylarylglycidyl ether or a mixture of these compounds.

The polyethylene glycols which can be used particularly according to the invention are polyethylene glycols with an average molecular weight of 1,000 to 20,000 and preferably 1,500 to 10,000.

The compounds corresponding to the formula II are preferably used in a molar ratio of 1 to 4:1 and more preferably 1.5 to 3:1 relative to the hydroxyl end groups of the polyethylene glycols.

The basic catalysts which are more particularly preferred in the process for the preparation of the products are alkali metal catalysts such as sodium, potassium, sodium methylate or ethylate or potassium methylate or ethylate, sodium hydroxide or potassium hydroxide.

These catalysts are suitably used in molar proportions of 10 to 300% and preferably 20 to 100%, relative to the polyethylene glycols.

The polyaddition reactions of the compounds of the formula (II) to the polyethylene glycols are generally carried out under an inert atmosphere and preferably under a nitrogen atmosphere, at a temperature of, say, 120° to 180° C.

After neutralisation of the catalyst with hydrochloric acid, if appropriate, the addition products are usually in the form of white or slightly coloured waxes which are soluble or dispersible in water at a concentration of more than 20%, with gelling.

If these products are used at lower concentrations, a separation into two phases is observed, one phase being gelled and containing the products according to the invention, and the other virtually consisting of water. However, it is possible to prepare homogeneous compositions containing the products of the invention at concentrations of, say, 0.2 to 10% and preferably of 1 to 3% by weight, in the presence of one or more surface-active agents chosen from non-ionic, anionic, cationic, amphoteric or zwitterionic surface-active agents, or mixtures thereof, the proportion by weight of the products according to the invention varying from, say, 5 to 40%, relative to the surface-active agents. In this case, the products according to the invention make it possible to obtain limpid or slightly opalescent, aqueous solutions of substantially increased viscosity.

Because of their properties, the products according to the invention can be used as thickeners, in particular in cosmetics and in pharmacy, in the proportions mentioned.

The cosmetic and/or pharmaceutical compositions which form a further aspect of the present invention are essentially characterised in that they contain at least one product corresponding to the formula (I), together with a cosmetically and/or pharmaceutically active ingredient.

In general, the cosmetic and/or pharmaceutical compositions according to the invention are in the form of viscous liquids, gels, dispersions, creams or pastes.

In one embodiment, the cosmetic and/or pharmaceutical compositions according to the invention contain from 0.2 to 10% and preferably from 1 to 3% of the product according to the invention, in the presence of one or more surface-active agents which are non-ionic, anionic, cationic, amphoteric or zwitterionic derivatives, or mixtures thereof, the proportion by weight of the compounds according to the invention preferably being from 5 to 40%, relative to the surface-active agents.

The cosmetic compositions include, in particular, compositions intended for the care of the skin, nails and hair, which can also contain, for example, surface-active products, alkalising or acidifying agents, foam synergistic agents and foam stabilisers, other thickeners, opacifiers, sequestering agents, superfatting agents, antiseptics, preservatives, anionic, cationic, non-ionic or amphoteric polymers, pigments, perfumes, dyestuffs, agents for imparting pearlescence, solvents, sun filters, oxidising agents, reducing agents, electrolytes, oils, waxes, natural substances, protein derivatives, anti-seborrhoea agents, anti-dandruff agents and any other active substance which can have an action in the treatment, care or protection of the skin or hair, and any other adjuvant normally used in cosmetic compositions.

The compositions according to the invention can, in particular, be used as shampoos, foam baths, liquid soaps and lotions or creams to be applied before or after shampooing, before or after dyeing or bleaching or before or after permanent waving.

The compositions can also be used for dyeing or bleaching the hair, as creams or milks for the body or as make-up products. They can contain, in addition to the products of the present invention, other ingredients conventionally used in these types of composition.

The acids and the bases are generally used in amounts so as to adjust the pH of the compositions to 3 to 12 and preferably 3 to 10.

The pharmaceutical compositions also contain active substances intended for the treatment of the human or animal body and pharmaceutically acceptable excipients.

The following Examples further illustrate the present invention.

PREPARATION EXAMPLE (I)

5.8 g of sodium methylate containing 5.64 milliequivalents/g (33 milliequivalents) are added to 150 g (0.075 mol) of polyethylene glycol 2,000 (P.E.G. 2,000) molten at 90° C., under a nitrogen atmosphere, and the mixture is then heated gradually to 150° C., the methanol being removed at ordinary pressure and then under reduced pressure.

54 g (0.225 mol) of 1,2-epoxyhexadecane are then introduced dropwise, at 150°–155° C., in the course of about 40 minutes.

The heating and the stirring are maintained for 1 hour after the addition has ended.

The degree of completion of the reaction, assessed by determining the remaining epoxide groups, is 97.5%.

The basicity introduced is neutralised by adding 33 ml of normal hydrochloric acid.

After drying by heating under reduced pressure, a light yellow wax melting at 29° C. is obtained.

The compound obtained corresponds to the following formula:

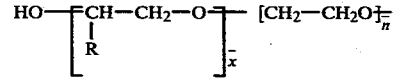

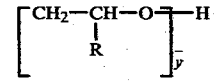

$R = C_{14}H_{29}$ $\bar{n} \simeq 45 \quad \overline{x+y} = 3$

The other compounds of the invention, shown in Table 1 which follows, are prepared in the same way; this table indicates the nature of the P.E.G., the nature of the epoxide compound of the formula II together with the amounts used, the molar ratios of the compounds of the formula II to the P.E.G., and the amounts of sodium methylate, expressed in milliequivalents per gram.

TABLE 1

PREPARATION OF THE COMPOUNDS OF THE FORMULA (I)

| | P.E.G. | | $R-CH-CH_2$ (II) $\setminus O /$ | | Molar ratio | Sodium methylate (milli- |
|---------|-------------------|---------------|-------------|---------------|----------------|-----------------|
| Example | Molecular weight | Weight (g) | R | Weight (g) | II/P.E.G. | equivalents) |
| 1 | 2,000 | 150 | $C_{14}H_{29}$ | 54 | 3 | 33 |
| 2 | 3,000 | 900 | $C_{14}H_{29}$ | 216 | 3 | 132 |
| 3 | 3,000 | 180 | $C_{10}H_{21}$ | 44 | 4 | 28 |
| 4 | 3,000 | 150 | $C_{10}H_{21}$ | 55 | 6 | 24 |
| 5 | 4,000 | 180 | $C_{14}H_{29}$ | 32.5 | 3 | 20 |
| 6 | 4,000 | 200 | $C_{14}H_{29}$ | 48 | 4 | 15 |
| 7 | 6,000 | 180 | $C_{10}H_{21}$ | 22 | 4 | 14 |
| 8 | 6,000 | 180 | $C_{10}H_{21}$ | 33 | 6 | 14 |
| 9 | 6,000 | 180 | $C_{16}H_{33}$ | 24 | 3 | 14 |
| 10 | 4,000 | 200 | $R_1-O-CH_2$ | 44.7 | 3 | 22 |
| 11 | 4,000 | 100 | $R_2-O-CH_2$ | 28 | 3 | 25 |
| 12 | 10,000 | 73 | $R_3-O-CH_2$ | 10.3 | 4 | 16 |
| 13 | 3,000 | 45 | $R_4-OCH_2$ | 10.2 | 3 | 6.6 |
| 14 | 20,000 | 100 | $C_{14}H_{29}$ | 9.6 | 8 | 2 |

$R_1$ = hexadecyl
$R_2$ = oleyl
$R_3$ = 2-ethylhexyl
$R_4$ = $CH_2=CH(CH_2)_9-$

TABLE II

CHARACTERISTICS OF THE COMPOUNDS OF THE FORMULA (I)

| Example | $\bar{n}$ | $x+y$ | R | Melting point |
|---------|-----|-------|---|---------------|
| 1 | 45 | 3 | $C_{14}H_{29}$ | 29° C. |
| 2 | 68 | 3 | $C_{14}H_{29}$ | 42° C. |
| 3 | 68 | 4 | $C_{10}H_{21}$ | 36° C. |
| 4 | 68 | 6 | $C_{10}H_{21}$ | 34° C. |
| 5 | 90 | 3 | $C_{14}H_{29}$ | 37° C. |
| 6 | 90 | 4 | $C_{14}H_{29}$ | 35° C. |
| 7 | 136 | 4 | $C_{10}H_{21}$ | 48° C. |
| 8 | 136 | 6 | $C_{10}H_{21}$ | 44° C. |
| 9 | 136 | 3 | $C_{16}H_{33}$ | 52° C. |
| 10 | 90 | 3 | $R_1-O-CH_2-$ $R_1$ = hexadecyl | 36° C. |
| 11 | 90 | 3 | $R_2-O-CH_2-$ $R_2$ = oleyl | 40° C. |
| 12 | 227 | 4 | $R_3-O-CH_2-$ $R_3$ = 2-ethylhexyl | 53° C. |
| 13 | 68 | 3 | $CH_2=CH(CH_2)_9OCH_2$ | 42° C. |
| 14 | 454 | 8 | $C_{14}H_{29}$ | 55° C. |

COMPOSITION EXAMPLES

EXAMPLE 1

Shampoo

| | |
|---|---|
| Product of Example 7 | 3 g |
| Copra bis-(2-hydroxyethyl)-amine oxide containing 39% of active ingredient, sold under the name AROMOX C/12 W by AKZO | 5 g |
| Sorbitan monolaurate oxyethyleneated with 20 mols of ethylene oxide, sold under the name TWEEN 20 by ATLAS | 10 g |
| Quaternised cellulose derivative sold under the name JR. 400 by UNION CARBIDE | 0.5 g |
| Water, preservative, perfume, dyestuff q.s.p. | 100 g |

The pH is adjusted to 7 with NaOH.
The viscosity, measured with a Ford cup of diameter 2 mm, is 2 minutes 15 seconds.

This composition is in the form of a thick liquid. It is used as a shampoo. It is found to be unctuous and to adhere well to the hair.

EXAMPLE 2

Shampoo

| | |
|---|---|
| Product of Example 8 | 2 g |
| $C_{12}$–$C_{18}$—alkyl-dimethylcarboxymethylammonium hydroxide containing 30% of active ingredient, sold under the name DEHYTON AB 30 by HENKEL | 10 g |
| Sodium salt of sulphated lauryl alcohol oxyethyleneated with 5 mols of ethylene oxide, containing 25% of active ingredient, sold under the name SIPON LFS 525 by SINNOVA | 10 g |
| Poly-[N—[3-(dimethylammonio)-propyl]-N'—[3-ethylene-oxyethylene-(dimethylammonio)-propyl]-urea] dichloride sold under the name MIRAPOL A 15 by MIRANOL | 1 g |
| Water, perfume, preservative, dyestuff q.s.p. | 100 g |

The pH is adjusted to 6.5 with NaOH.
The viscosity, measured with a Ford cup of diameter 2 mm, is 58 seconds.
Applied to the hair, the composition is unctuous and adheres well to the hair.

EXAMPLE 3

Shampoo in Gel Form

| | |
|---|---|
| Product of Example 2 | 5 g |
| Sodium salt of sulphated alkanol ($C_{12}$–$C_{14}$) oxyethyleneated with 2.2 mols of ethylene oxide (25% of active ingredient) | 25 g |
| Adipic acid/dimethylaminohydroxypropyl-diethylene-triamine copolymer sold under the name CARTARETINE F.4 by SANDOZ | 0.8 g |
| Water, perfume, dyestuff, preservative q.s.p. | 100 g |

The pH is adjusted to 8.5 with HCl.
This composition is unctuous and does not run when it is applied to the hair.

EXAMPLE 4

Shampoo in Gel Form

| | |
|---|---|
| Product of Example 8 | 9 g |
| Sodium salt of sulphated alkanol ($C_{12}$–$C_{14}$) oxyethyleneated with 2.2 mols of ethylene oxide (25% of active ingredient) | 25 g |
| Dimethyldiallylammonium chloride/acrylamide copolymer sold under the name MERQUAT 550 by MERCK | 0.3 g |
| Water, perfume, dyestuff, preservative q.s.p. | 100 g |

The pH is adjusted to 5 with NaOH.

As previously, a good adhesion to the hair is found.

EXAMPLE 5

Shampoo in Fluid Gel Form

| | |
|---|---|
| Product of Example 7 | 5 g |
| Sodium salt of sulphated alkanol ($C_{12}$–$C_{14}$) oxyethyleneated with 2.2 mols of ethylene oxide, containing 25% of active ingredient | 15 g |
| Vinylpyrrolidone/dimethylaminoethyl methacrylate copolymer quaternised by dimethyl sulfate, sold under the name GAFQUAT 755 by G.A.F. | 0.3 g |
| Surface-active agent of the formula: $R(OCH_2CH_2)_{10}-O-CH_2-COOH$, R being a mixture of $C_{12}$–$C_{14}$ alkyl radicals, sold under the name AKYPO RLM 100 by CHEM-Y | 5 g |
| Water, perfume, preservtive q.s.p. | 100 g |

The pH is adjusted to 6 with NaOH.

The fluid gel is unctuous and perfect to apply to the hair.

EXAMPLE 6

Shampoo

| | |
|---|---|
| Product of Example 7 | 2 g |
| Triethanolamine alkyl ($C_{12}$–$C_{14}$)-sulphate containing 40% of active ingredient | 25 g |
| Water, perfume, dyestuff, preservative q.s.p. | 100 g |

The pH is adjusted to 7.3 with NaOH.

The shampoo is easy to apply and does not run into the eyes.

EXAMPLE 7

Shampoo

| | |
|---|---|
| Product of Example 7 | 2 g |
| Cycloimidazoline derivative of coconut oil, containing 38% of active ingredients, sold under the name MIRANOL C 2M by MIRANOL | 10 g |
| Water, perfume, dyestuff, preservative q.s.p. | 100 g |

The pH is adjusted to 8 with HCl.

The shampoo has an unctuous consistency and holds well on the hair.

EXAMPLE 8

Shampoo

| | |
|---|---|
| Product of Example 2 | 2 g |
| Surface-active agent of the formula: $RCHOHCH_2O-(CH_2CHOHCH_2O)_nH$, R being a mixture of $C_9$–$C_{12}$ alkyl radicals and n being equal to 3.5 (statistical value) | 10 g |
| Water, perfume, dyestuff, preservative q.s.p. | 100 g |

The pH is adjusted to 7.2 with HCl.

Results similar to those observed in Example 7 are found.

EXAMPLE 9

Rinse in Thick Gel Form

| | |
|---|---|
| Product of Example 2 | 5 g |
| Sorbitan monolaurate oxyethyleneated with 20 mols of ethylene oxide, sold under the name TWEEN 20 by ATLAS | 5.5 g |
| Vinylpyrrolidone/dimethylaminoethyl methacrylate copolymer quaternised by dimethyl sulphate, sold under the name GAFQUAT 755 by G.A.F. | 0.3 g |
| Stearyldimethylbenzylammonium chloride sold under the name AMMONYX 4002 by FRANCONYX | 5 g |
| Water, preservative, perfume, dyestuff q.s.p. | 100 g |

The pH is adjusted to 8 with NaOH.

The composition is unctuous and adheres well to the hair to which it is applied, without running onto the face.

EXAMPLE 10

Thickened Limpid Shampoo

The following composition is prepared:

| | |
|---|---|
| Product of Example 2 | 1.3 g |
| (Coconut amidopropyl)-dimethylamine oxide containing 30% of active ingredient, sold under the name AMMONYX CDO by FRANCONYX | 30 g |
| Sodium salt of sulphated alkanol ($C_{12}$–$C_{14}$) oxyethyleneated with 2.2 mols of ethylene oxide, containing 25% of active ingredient | 20 g |
| Water, preservatives, dyestuffs q.s.p. | 100 g | pH = 7.5 with hydrochloric acid.

The viscosity of this composition at 20° C. is 25,000 cps.

Applied to wet hair, this shampoo gives a copious, firm, stable and mild foam.

The product of this invention serves two purposes here, namely that of a thickener and that of a foam synergistic agent.

EXAMPLE 11

Thickened Liquid Soap

| | |
|---|---|
| Sodium isethionate fatty esters sold under the name FENOPON AC 75 by GAF | 10 g |
| Product of Example 2 | 2 g |
| Water q.s.p. | 100 g |

EXAMPLE 12

Thickened Liquid Soap

| | |
|---|---|
| Triethanolamine salt of the condensation product of copra fatty acids and protein hydrolysates sold under the name MAYPON 4 CT by SEPPIC | 10 g |
| Sorbitan monolaurate oxyethyleneated with 20 moles of ethylene oxide sold under the name TWEEN 20 by ATLAS | 1 g |
| hexamidine diisethionate | 0.05 g |
| Product of Example 2 | 2 g |

-continued

| | |
|---|---|
| Water q.s.p. | 100 g |

In both cases a thickened liquid soap is obtained which is soft to the skin.

EXAMPLE 13

Moisturising Day Cream

| | |
|---|---|
| Sodium stearate | 2 g |
| Oil of the formula: | 30 g |
| $C_{15}H_{31}$—COO—$CH_2$—CH—$CH_2$—O—$CH_2$—CH—$C_4H_9$ | |
| $\quad\quad\quad\quad\quad\quad\quad\quad$ OH $\quad\quad\quad\quad\quad\quad\quad$ $C_2H_5$ | |
| prepared according to Example 5 of French Specification No 2 222 351 | |
| Oil of grape pips | 10 g |
| Sodium lactate | 1 g |
| Glycerine | 2 g |
| Product of Example 4 | 10 g |
| Preservations | qs |
| Antioxidants | qs |
| Perfume | qs |
| Sterile demineralized water q.s.p. | 100 g |

EXAMPLE 14

Colour Base

| | |
|---|---|
| Product of Example 2 | 10 g |
| Myrj 53 | 5 g |
| Isopropyl palmitate | 15 g |
| Liquid petrolatum | 15 g |
| Cetiol LC | 5 g |
| Pigments | qs |
| Preservatives | qs |
| Perfume | qs |
| Sterile demineralised water q.s.p. | 100 g |

EXAMPLE 15

Mascara Cream

| | |
|---|---|
| Triethanolamine stearate | 10 g |
| Candelilla wax | 15 g |
| Beeswax | 17 g |
| Xanthan gum | 0.95 g |
| Product of Example 4 | 1 g |
| Black iron oxide | 5 g |
| Aminosilicate polysulfide | 4 g |
| Softened water q.s.p. | 100 g |

EXAMPLE 16

Body Milk

| | |
|---|---|
| Product of Example 2 | 4 g |
| Propylene glycol | 4 g |
| Triethanolamine stearate | 2 g |
| Oil of the formula: | 25 g |
| $C_{15}H_{31}$—COO—$CH_2$—CH—$CH_2$—O—$CH_2$—CH—$C_4H_9$ | |
| $\quad\quad\quad\quad\quad\quad\quad\quad$ OH $\quad\quad\quad\quad\quad\quad\quad$ $C_2H_5$ | |
| prepared according to Example 5 of French Specification No 2 222 351 | |
| Soft Almond oil | 5 g |
| Methyl parahydroxybenzoate | 0.30 g |
| Perfume | qs |
| Sterile demineralized water q.s.p. | 100 g |

EXAMPLE 17

Nourishing Cream

| | |
|---|---|
| Brij 96 | 10 g |
| Product of Example 8 | 7 g |
| Maize oil | 13 g |
| Sunflower oil | 13 g |
| Oil of the formula: | 5 g |
| $C_{15}H_{31}$—COO—$CH_2$—CH—$CH_2$—O—$CH_2$—CH—$C_4H_9$ | |
| $\quad\quad\quad\quad\quad\quad\quad\quad$ OH $\quad\quad\quad\quad\quad\quad\quad$ $C_2H_5$ | |
| Propylene glycol | 3 g |
| Preservatives | qs |
| Antioxidants | qs |
| Perfume | qs |
| Sterile demineralized water q.s.p. | 100 g |

EXAMPLE 18

Toilet Cream

| | |
|---|---|
| Glycerol monostearate | 5 g |
| TWEEN 20 | 5 g |
| Product of Example 2 | 10 g |
| Propylene glycol | 5 g |
| Cetiol LC | 10 g |
| Oil of the formula: | 10 g |
| $C_{15}H_{31}$—COO—$CH_2$—CH—$CH_2$—O—$CH_2$—CH—$C_4H_9$ | |
| $\quad\quad\quad\quad\quad\quad\quad\quad$ OH $\quad\quad\quad\quad\quad\quad\quad$ $C_2H_5$ | |
| prepared according to Example 5 of French Specifications No 2 222 351 | |
| Preservatives | qs |
| Perfume | qs |
| Sterile demineralized water q.s.p. | 100 g |

EXAMPLE 19

Hair Lotion

The following lotion is prepared:

| | |
|---|---|
| $C_{12}$–$C_{18}$ alkyldimethylcarboxymethyl ammonium hydroxide containing 30% of acitve ingredient, sold under the name DEHYTHON AB 30 by HENKEL | 30 g |
| Cationic polymer of the formula | |
| $\left[\begin{array}{c}CH_3\\|\\-N^{\oplus}-(CH_2)_3-N^{\oplus}-(CH_2)_6-\\|\quad Cl^{\ominus}\quad\quad|\quad Cl^{\ominus}\\CH_3\quad\quad\quad\quad CH_3\end{array}\right]$ | |
| which can be prepared as described in French Specification No 2 270 846 | 2 g |
| Quaternary vinylpyrrolidone copolymer having a molecular weight of 100,000 sold under the name GAFQUAT 734 by General Aniline (50% in ethyl alcohol) | 1 g |
| Product of Example 2 | 2 g |
| Triethanolamine q.s.p. | |
| Water q.s.p. | 100 g |

Application is made on sensitised hair after shampooing. It left for five minutes and then rinsed.

EXAMPLE 20

Foam Bath

| | |
|---|---|
| Isopropanolamine lauryl sulphate (45% active ingredient) | 15.0 g |
| Sodium lauryl ether sulphate with 2 moles of ethylene oxide (25% active ingredient) | 45.0 g |
| Fatty amine derivatives having a betaine structure | |

-continued

| | |
|---|---|
| (30% active ingredient) | 5.0 g |
| Product of Example 2 | 2.5 g |
| Glycol distearate | 2.0 g |
| Preservative | 0.3 g |
| Perfume | |
| Water q.s.p. | 100 g |

EXAMPLE 21

Foam Bath

| | |
|---|---|
| Sodium lauryl ether sulphate with 2 moles of ethylene oxide (25% active ingredient) | 60.0 g |
| Fatty amine derivatives of betaine structure (30% active ingredient) | 2.5 g |
| Oleyl sarcosine | 1.5 g |
| $C_{12}$–$C_{18}$ alkyl aminopropyl dimethyl aminooxide (35% active ingredient) | 5.0 g |
| Product of Example 2 | 2.5 g |
| Glycol distearate | 0.75 g |
| Quaternary vinyl pyrrolidone copolymer of molecular weight 1,000,000 sold under the name GAFQUAT 755 by GAF (20% active ingredient) | 2.5 g |
| Methyl parahydroxybenzoate | 0.3 g |
| Water q.s.p. | 100 g |

EXAMPLE 22

Aerosol Shaving Foam

The following composition is prepared:

| | |
|---|---|
| Stearine | 5.45 g |
| Myristic acid | 1.20 g |
| Triethanolamine | 3.70 g |
| Glycerine | 5.00 g |
| Cycloimidazoline derivative of coconut oil (40% active ingredient) sold under the name MIRANOL C2M Conc by MIRANOL | 0.50 g |
| Lanolinic acid | 0.50 g |
| Product of Example 2 | 0.25 g |
| Perfume | 0.70 g |
| Water q.s.p. | 100 g |

This composition is made into an aerosol has 96% active ingredient and 4% hydrocarbons as propellant.

EXAMPLE 23

Toilet Soap

| | | |
|---|---|---|
| Flakes - { | Pork fat | 94.33 g |
| | Copra oil | |
| Soft almond oil | | 2.00 g |
| Product of Example 2 | | 1.00 g |
| Titanium dioxide | | 0.10 g |
| Ethylene diamine tetraacetic acid | | 0.05 g |
| Butylhydroxytoluene | | 0.02 g |
| Perfume | | 2.50 g |

EXAMPLE 24

Dermatological Block

| | |
|---|---|
| Fatty acid esters of sodium isethionate, the fatty acids being derived from copra, sold under the name FENOPON AC 78 by GAF | 60.00 g |
| White paraffin wax | 15.00 g |
| Polyethylene glycol 6000 | 2.00 g |
| Product of Example 2 | 1.00 g |
| Quaternary vinylpyrrolidone copolymer | |

-continued

| | |
|---|---|
| (20% in water) having a molecular weight of 1,000,000 sold under the name GAFQUAT 755 by GENERAL ANILINE | 3.50 g |
| Stearic acid monoethanolamide | 10.00 g |
| Glycerine | 5.00 g |
| Water | 1.30 g |
| Titanium dioxide | 0.20 g |
| Perfume | 2.00 g |

EXAMPLE 25

Direct Dye

The following composition is prepared:

| | |
|---|---|
| 1-hydroxy-2-amino-4,5-dinitrobenzene | 1.00 g |
| 1-amino-2-nitro-4-(N methylamino)benzene | 0.125 g |
| 1-hydroxy-3-nitro-4-aminobenzene | 0.03 g |
| 1-hydroxy-3-nitro-4-N—β-hydroxyethylaminobenzene | 0.45 g |
| Copra diethanolamide | 3.00 g |
| Lauryl alcohol with 12.5 moles of ethylene oxide | 10.00 g |
| Product of Example 2 | 2.00 g |
| Triethanolamine q.s.p. | |
| Water q.s.p. | 100 g |

This composition is applied to bleached hair. After leaving for 25 minutes, the hair is washed with water. A coppery shade is obtained.

EXAMPLE 26

Oxidation Cream

The following composition is prepared:

| | |
|---|---|
| 1-amino-4-(2-methoxyethyl)aminobenzene dihydrochloride | 1.60 g |
| Paraaminophenol | 0.30 g |
| Resorcinol | 0.20 g |
| Metaaminophenol | 0.25 g |
| 1-methyl-2-hydroxy-4-(2-hydroxyethyl)aminobenzene | 0.02 g |
| 1-(2-hydroxyethyloxy)-2,4-diaminobenzene dihydrochloride | 0.02 g |
| Copra diethanolamide | 3.00 g |
| Glycol distearate | 1.00 g |
| Sodium alkylether sulphate | 23.0 g |
| Sodium salt of diethylene triaminopentaacetic acid | 2.0 g |
| Product of Example 2 | 2.0 g |
| Ammonia, 22° B. | 10.0 g |
| Sodium bisulfite | 1 ml |
| Water q.s.p. | 100 g |

40 g of this composition are mixed with 40 g of 20 volume hydrogen peroxide. A thick cream is obtained which is applied to chestnut brown hair. It is left for 30 minutes and then the hair is rinsed. A deep ashen blond shade is obtained.

The commercial products represent the following materials:

| | |
|---|---|
| MYRJ 53 | Polyethylene glycol stearate (50 moles of ethylene oxide) sold by ATLAS |
| CETIOL LC | Cetyl laurate sold by HENKEL |
| BRIJ 96 | Oleic ether polyoxyethyleneated with 10 moles of ethylene oxide sold by ATLAS |
| TWEEN 20 | Sorbitan monolaurate oxyethyleneated with 20 moles of ethylene oxide sold by ATLAS. |

We claim:
1. A product having the formula

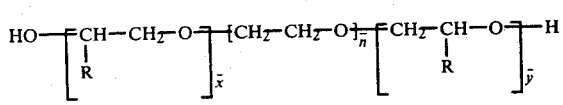

wherein each R represents, independently, alkyl having 8–18 carbon atoms, alkoxymethyl wherein the alkoxy moiety has 8–20 carbon atoms or alkenyloxy methyl wherein the alkenyl moiety has 8–20 carbon atoms, or a mixture thereof, $\bar{n}$ represents an average number from 20 to 500 and $\bar{x}$ and $\bar{y}$ independently represent an average number from 0 to 8 such that the sum $(\bar{x}+\bar{y})$ is from 1 to 8.

2. A product according to claim 1 in which $\bar{x}$ and $\bar{y}$ denote an average number of units from 1 to 8 such that $(\bar{x}+\bar{y})$ is from 2 to 8.

3. A product according to claim 1 in which $\bar{n}$ denotes an average number from 30 to 200.

4. A product according to claim 1 in which the proportion by weight of the oxyethyleneated part represents 70 to 95% of the total product.

5. A product having the formula

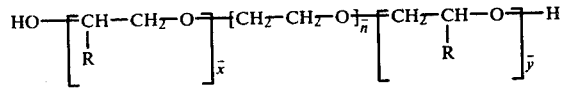

wherein each R represents independently alkyl having 8 to 18 carbon atoms or a mixture thereof, n represents an average number from 20 to 500 and $\bar{x}$ and $\bar{y}$ independently represent an average number from 0 to 8 such that the sum $(\bar{x}+\bar{y})$ is from 1 to 8.

6. The product of claim 5 wherein R is $C_{14}H_{29}$, n is 68 and $\bar{x}+\bar{y}$ is 3.

7. The product of claim 5 wherein R, n and the sum $(\bar{x}+\bar{y})$ are selected from the following combinations:
(a) R is $C_{14}H_{29}$, $\bar{n}$ is 45 and $\bar{x}+\bar{y}$ is 3,
(b) R is $C_{14}H_{29}$, $\bar{n}$ is 68 and $\bar{x}+\bar{y}$ is 3,
(c) R is $C_{10}H_{21}$, $\bar{n}$ is 68 and $\bar{x}+\bar{y}$ is 4,
(d) R is $C_{10}H_{21}$, $\bar{n}$ is 68 and $\bar{x}+\bar{y}$ is 6,
(e) R is $C_{14}H_{29}$, $\bar{n}$ is 90 and $\bar{x}+\bar{y}$ is 3,
(f) R is $C_{14}H_{29}$, $\bar{n}$ is 90 and $\bar{x}+\bar{y}$ is 4,
(g) R is $C_{10}H_{21}$, $\bar{n}$ is 136 and $\bar{x}+\bar{y}$ is 4,
(h) R is $C_{10}H_{21}$, $\bar{n}$ is 136 and $\bar{x}+\bar{y}$ is 6,
(i) R is $C_{16}H_{33}$, $\bar{n}$ is 136 and $\bar{x}+\bar{y}$ is 3, and
(j) R is $C_{14}H_{29}$, $\bar{n}$ is 454 and $\bar{x}+\bar{y}$ is 8.

* * * * *